United States Patent [19]

Dabi

[11] Patent Number: 4,645,789
[45] Date of Patent: Feb. 24, 1987

[54] CROSSLINKED CARBOXYL POLYELECTROLYTES AND METHOD OF MAKING SAME

[75] Inventor: Shmuel Dabi, Highland Park, N.J.

[73] Assignee: Personal Products Company, Milltown, N.J.

[21] Appl. No.: 770,477

[22] Filed: Aug. 29, 1985

Related U.S. Application Data

[63] Continuation-in-part of Ser. No. 604,709, Apr. 27, 1984, abandoned.

[51] Int. Cl.$^4$ .............................................. C08K 5/05
[52] U.S. Cl. .................................. 524/379; 524/389; 524/556; 524/559; 524/560; 521/97; 521/149; 525/375; 428/290; 128/156
[58] Field of Search ............... 524/379, 389, 556, 559, 524/560; 525/375; 521/97, 149

[56] References Cited

U.S. PATENT DOCUMENTS

| | | | |
|---|---|---|---|
| 3,806,498 | 4/1974 | Wilson et al. | 528/341 |
| 3,907,756 | 9/1975 | Marx et al. | 526/320 |
| 4,310,593 | 1/1982 | Gross | 428/260 |

FOREIGN PATENT DOCUMENTS 42-22044 10/1967 Japan.

Primary Examiner—Joseph L. Schofer
Assistant Examiner—N. Sarofim
Attorney, Agent, or Firm—Jason Lipow

[57] ABSTRACT

Crosslinked water absorbent carboxylic polyelectrolytes and articles made therefrom are provided. The polyelectrolytes are crosslinked using a di- or tri-functional aziridine crosslinking agent.

24 Claims, No Drawings

CROSSLINKED CARBOXYL POLYELECTROLYTES AND METHOD OF MAKING SAME

This application is a continuation-in-part of my co-pending application Ser. No. 604,709, filed on Apr. 27, 1984.

BACKGROUND OF THE INVENTION

This invention relates to highly absorbent and retentive materials for absorbing aqueous based fluids and more particularly for absorbing body fluids in such products as sanitary napkins, diapers, bandages and the like. Specifically, this invention is related to compositions and methods for preparing crosslinked polyelectrolytes capable of absorbing and retaining many times their weight of such aqueous fluids.

Highly absorbent crosslinked polyelectrolytes and methods of preparing the same are already known. U.S. Pat. Nos. 3,669,103 and 3,670,731 teach use of these materials in diapers and dressings. U.S. Pat. Nos. 2,988,539; 3,393,168; 3,514,419 and 3,557,067 teach methods of making such absorbents and in particular are related to water swellable crosslinked carboxylic copolymers that are either crosslinked during copolymerization or crosslinked after polymerization and then neutralized to result in pendant ionic moieties capable of imparting water retention properties to the finished material. Additionally polyelectrolytes have been prepared which are cured or crosslinked employing epihalohydrine. For example, U.S. Pat. No. 3,980,663 employ epihalohydrines but has been found to be unacceptably slow and inefficient as a method for crosslinking such polymers.

In U.S. Pat. No. 4,076,673 an improvement in the rate and efficiency of curing polyelectrolytes has been accomplished by employing as a crosslinking agent a polyamidepolyamine epihalohydrine adduct of the kind commercially available from Hercules, Incorporated and sold by them under the Trademark Polycup ®. A still further improvement in the choice of crosslinking agent is disclosed in U.S. Pat. No. 4,310,593 which teaches the use of monomeric amine epihalohydrine as a crosslinker which is said to have greater efficiency, longer shelf life and the convenience of being capable of shipping as a concentrate.

The above disclosures notwithstanding, there is still a need for improvement in crosslinked polyelectrolyte technology and in particular there is a need to improve the efficiency of the crosslinking reaction, the shelf life of the crosslinker and its convenience in use.

SUMMARY OF THE INVENTION

It has now been discovered that a crosslinker may be employed to cure or crosslink polyelectrolytes which exhibits significantly greater efficiency, faster reaction rate and greater shelf life without sacrificing any of the advantages of prior suggested processes.

In particular it has been discovered that these desirable attributes may be achieved by employing in such compositions and methods a crosslinking agent which is a water soluble, relatively low molecular weight compound having at least two 1-aziridinyl groups bonded thereto. Preferably, such groups have the general formula:

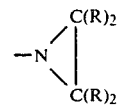

wherein each R group is independently selected from the group consisting of H, alkyl having from one to three carbon atoms, or alkylene having from one to three carbon atoms. Preferably the compound has a molecular weight of less than 1000. Of choice the functional groups are bonded to aliphatic or substituted aliphatic groups sufficiently small enough to maintain the compound soluble in water. The crosslinkers of choice are di- and tri-functional aziridine several of which are commercially available.

It has been found that employment of the crosslinking agents of this invention results in the ability to use only minimal amounts of crosslinking agents, that the curing rates of these agents are demonstratably faster than prior agents and that the shelf life of these agents, notwithstanding their higher reactivity, are substantially longer than prior agents.

DETAILED DESCRIPTION OF THE INVENTION

The carboxylic polyelectrolytes capable of being crosslinked in accordance with the teachings of this invention are well-known and are described in detail in U.S. Pat. No. 4,310,593 which is incorporated herein by reference. The essence of usable polyelectrolytes is that they comprise, at least in the salt form, sufficient carboxylate moieties to render them water soluble. Usable polymers, capable of being prepared from readily available monomers and converted into their salt form include for example, acrylic acid-acrylate copolymers; acrylic acid-acrylamide copolymers; acrylic acid-olefin copolymers; polyacrylic acid; acrylic acid-vinyl aromatic copolymers; acrylic acid-styrene sulfonic acid copolymers; acrylic acid-vinyl ether copolymers; acrylic acid vinyl acetate copolymers, acrylic acid-vinyl alcohol copolymers; copolymers of methacrylic acid with all of the above comonomers; copolymers of maleic acid, fumaric acid and their esters with all of the above comonomers; copolymers of maleic anhydride with all of the above comonomers.

The conversion to the salt form may take place either before or after the crosslinking reaction, but in any event, the crosslinked polyelectrolyte should have at least 25% of the carboxyl groups, on a molar basis, in the salt form.

Generally described, the crosslinking agents of this invention are low molecular weight, water soluble compounds having at least two 1-aziridinyl groups bonded thereto which groups preferably have the general formula:

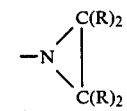

wherein the R groups may be independently selected from the group comprising H, alkyl having from one to three carbon atoms or alkenyl having from two to three carbon atoms. The functional groups are preferably bonded to an aliphatic chain or a substituted aliphatic chain with the essential criterion that such chains be small enough to insure that the compound is water soluble. Preferably the compound has a molecular weight of less than 1000. Such aliphatic or substituted aliphatic chains may include olefinic groups from 2 to 12 carbon atoms; substituted olefinic groups such as olefinic hydroxides, e.g., butylenehydroxide or butylenedihydroxide; mercaptans of olefins such as mercaptobutylene; ethers of aliphatic compounds such as diethylene glycol or triethylene glycol; esters of aliphatic compounds such as triglycerides or esters of trimethylpropane and pentaerythritol.

Several such compounds are already commercially available and it will be understood by one skilled in the art that a great many variations of these commercially available compounds can be synthesized while still conforming to the general description given above. A particularly effective group of compounds are the triaziridines based on trimethylolpropane tripropionates having the formula:

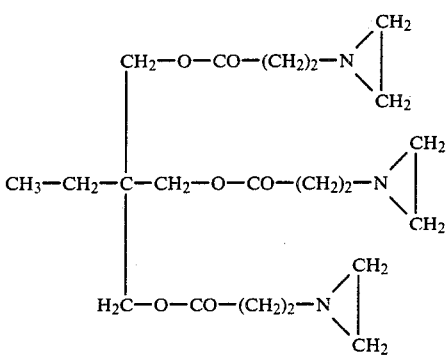

and sold by the Aceto Chemical Company under the trade name TAZ.

Another effective compound, based on pentaerythritol tripropionate adduct, has the formula:

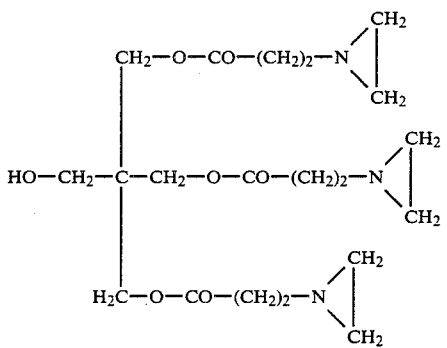

and is sold by Aceto Chemical Company under the trade name TAZO. Similar materials conforming to the general description given above are available from Cordova Chemical Company under the trade name XAMA. Additionally, other polyfunctional aziridines that have triazine or phosphate backbones are also available. Such are, for example, tris(1-aziridinyl)phosphine oxide, tris(1-aziridinyl)-phosphine sulfide; 2,4,6,trisaziridinyl-s-triazine.

The reaction of the functional group of the aziridine with the carboxyl group of a carboxylic polyelectrolyte proceeds rapidly at temperatures of from room temperature or less to about 150° C. with, of course, increasing reaction rate the highest temperatures. The reaction proceeds through ring opening as follows:

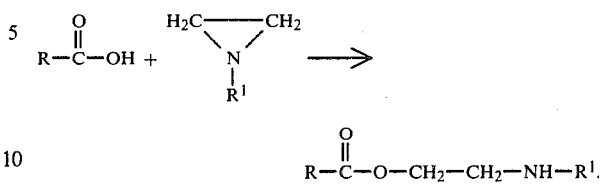

Crosslinking takes place when a polyfunctional aziridine molecule reacts as above with carboxyl groups of adjacent polyelectrolytes to form bridges between these molecules.

In the general method of carrying out this invention, a solution is prepared comprising from 5 to 60% by weight of a carboxylic polyelectrolyte, e.g., polyacrylic acid or salts thereof having molecular weights which may vary from 10,000 to 4,000,000 or more. Preferably such molecular weights should range from 10,000 to 1,000,000. As used in this connection, the term "molecular weight" is meant to denote the weight average molecular weight of the polymer. The choice of molecular weight for the polyelectrolyte may vary over this wide range depending on the desired properties of the finished crosslinked product. For example, extremely low weight polyelectrolytes will go into solution easily and hence highly concentrated solutions may be prepared which will require less drying to produce the final product. Low weight polyelectrolytes however require a higher ratio of crosslinking agent to insolubilize. On the other hand, extremely high molecular weight polyelectrolytes form very viscous solutions which are difficult to handle in their pre-crosslinked form but require lower concentration of crosslinking agent to insolubilize.

The solvent of choice is water although other solvents such as alcohol or mixtures of water and alcohol may be employed.

The solution may be maintained in the acid state and neutralization may take place after crosslinking or the solution may be neutralized to as high a pH as 12 or more utilizing a strong base such as sodium hydroxide. Preferably the reaction is best controlled when preparing a relatively neutral solution in the range of from 5 to 10 pH and still more preferably in the range of from 6 to 8.

The polyfunctional aziridine is dissolved into the solution at a concentration which may vary from about 0.2 to about 20% by weight, based on the weight of the carboxylic polyelectrolyte. Preferably, the concentration should range from 0.5 to 15% and still more preferably from 1 to 10%. For a given polyelectrolyte, too low a concentration of aziridine will result in a failure to render the polyelectrolyte insoluble. On the other hand, too high a concentration of aziridine will result in a crosslinked product which exhibits relatively low swelling and hence low absorption capacity. These properties also vary with the molecular weight of the uncrosslinked polymer wherein a greater concentration of crosslinking agent is required to insolubilize a low molecular weight polyelectrolyte and a lesser quantity of crosslinker may be employed with higher molecular weight polyelectrolytes. In general, to obtain best absorption properties, the minimum quality of crosslinking agent capable of insolubilizing the polyelectrolyte should be employed.

The solution may be cast onto a release substrate to produce a highly absorbent film upon drying. The film may then be crushed to form an absorbent powder, the common form of highly absorbent materials suggested for use in such body fluid absorbent products as diapers, sanitary napkins, tampons, dressings or the like.

A particularly useful material may be produced by employing, as the neutralizing base, a carbonate compound such as $Na_2CO_3$, $K_2CO_3$ or ammonium bicarbonate. The neutralization of the carboxylic polyelectrolyte will release carbon dioxide gas and foam the mixture which, on drying, produces a cellular, foam-like material having high volume and enhanced absorbency. Ordinarily, it would be difficult to use such a system to foam the polymers as the cells tend to collapse too quickly. However, because of the rapidity of reaction with the crosslinking agents of this invention this is now possible.

Another method of utilizing the compositions and methods of the invention is to spray the solution of polyelectrolytes and crosslinkers onto the surface of a substrate such a tissue which when dried will exhibit good absorption properties. Alternatively, the solution may be applied by padding or saturating a substrate such as a pad of cellulose fibers or the like which then may be dried, with the highly absorbent crosslinked polyelectrolyte distributed throughout the pad. Vacuum suction means can be employed to control the solution add-on as is currently employed for producing suction bonded nonwoven fabrics. The dried crosslinked polyelectrolyte adheres to most surfaces with sufficient tenacity to preclude problems such as sifting or dislocation typically encountered when attempting to combine absorbent powders with nonwoven fabrics or pads of cellulosic materials.

EXAMPLE 1

A composition is prepared by mixing a 25%, by weight, aqueous solution of poly (sodium acrylate) having a molecular weight of 100,000 with a sufficient quantity of 50% by weight of aqueous sodium hydroxide to neutralize to a pH of from 7 to 8. The triaziridine based on trimethylolpropane tripropionate, TAZ, and obtained from the Aceto Chemical Company, is dissolved into the solution in various concentrations, as are set out in Table 1 below in percent by weight, based on the weight of the poly(sodium acrylate). A film of the solution, 30 mils thick is cast onto silicon coated paper and dried in an oven at 110° C. for 30 minutes. The films are peeled from the paper and ground to 20 mesh powders. The weighed powders are saturated with test fluids (deionized water and a 1% by weight aqueous NaCl solution), excess fluid is absorbed with paper towels and the weight gain of water is measured as the Free Absorbency. The results are reported below in Table 1.

TABLE 1

| Crosslinker (TAZ), % | Free Absorbency, g/g | |
|---|---|---|
| | Water | 1% NaCl |
| 0.5 | soluble | — |
| 1.2 | 75 | 12 |
| 2.0 | 128 | 22 |
| 4.0 | 70 | 10 |
| 7.0 | 10 | — | can be seen from the above table, this relatively low molecular weight polyelectrolyte reached an optimum Free Absorbency value at approximately 2% crosslinker concentration and thereafter exhibited reduced absorbency.

EXAMPLE 2

The precedure of Example 1 is followed with the exception that a 200,000 molecular weight poly (sodium acrylate) was employed. The crosslinker used for this Example 2 is the triaziridine based on pentaerythritol tripropionate adduct, TAZ-0, sold by the Aceto Chemical Company. The results are shown in Table 2 below.

TABLE 2

| Crosslinker (TAZ-0), % | Free Absorbency, g/g | |
|---|---|---|
| | Water | 1% NaCl |
| 8 | 60 | — |
| 4 | 70 | — |
| 2 | 140 | 35 |
| 1 | 330 | 45 |
| 0.6 | —soluble— | |

As can be seen, this relatively high molecular weight polyelectrolyte exhibited optimum absorbency at about 1% crosslinker concentration.

EXAMPLE 3

The procedure of Example 1 is repeated with the exception that the polyelectrolyte employed was poly(acrylic acid) neutralized with sodium hydroxide and having varying molecular weights as set out in Table 3 below and the crosslinking agent employed is TAZ-0 at a constant concentration of 1%. As in Example 1 a 25% solution of the polyelectrolyte is employed with the exception that, for the 400,000 molecular weight polyacrylic acid, a 12.5% solution is used. The results are reported below in Table 3.

TABLE 3

| Poly(acrylic acid) Molecular Weight | Free Absorbency (g/g) | |
|---|---|---|
| | Water | 1% NaCl |
| 25,000 | —soluble— | |
| 60,000 | 130 | 29 |
| 200,000 | 360 | 40 |
| 400,000 | 435 | 43 |

As can be seen from this example, for the constant value of crosslinker concentration, absorbency increased with increasing molecular weight.

EXAMPLE 4

A crosslinked absorbent polyelectrolyte foam is prepared. A mixture of three grams of sodium hydroxide, three grams of potassium carbonate, and one gram of ammonium bicarbonate are dissolved in 80 grams of water and one gram of the TAZ triaziridine crosslinking agent. The solution is poured on 10 grams of 450,000 molecular weight polyacrylic acid powder obtained from Polysciences, Inc. and hand mixed thoroughtly for three minutes. The mixture has a dough-like consistency due to the carbon dioxide released from the carbonate compounds. The mixture is heated for 30 seconds in a microwave oven and then kept for 15 minutes in a hot air oven at 120° C. The resulting dry material is fluffy and cellular and demonstrates a very high absorption rate. The material is crushed manually and the free absorbency is measured as described above. The material is found to absorb 480 grams per gram of deionized water and 55 grams per gram of one percent, by weight, sodium chloride aqueous solution.

EXAMPLE 5

A crosslinked polyelectrolyte absorbent film is produced. A 25 percent aqueous solution of polyacrylic acid having a molecular weight of 100,000 and obtained from the North Chemical Inc. Company in the quantity of 26.4 grams was neutralized with four grams of potassium carbonate and two grams of ammonium bicarbonate. Two drops of a surfactant, pluronic L-62, was added to break up the foam. The crosslinker, TAZ triaziridine, was mixed into the solution and a film was cast on a silicone coated paper. After 15 minutes, at 110° C., a strong but brittle film was obtained that swelled instantly when wetted by water. The film was crushed in a mortar and the powder had a free absorbency of 128 grams per gram of water and 22 grams per gram of one percent sodium chloride solution. Measurements for absorption retention under pressure were taken using the gravimetric absorbency tester (GAT) instrument, described in U.S. Pat. No. 4,357,827. The absorption using this instrument was found to be 20.8 grams per gram with a retention of 14.8 grams per gram using a 1%, by weight, aqueous sodium chloride test fluid.

EXAMPLE 6

The formulation of Example 5 was diluted with water to give a 10 percent by weight solid solution. Solution was sprayed onto a non-woven fabric of cellulosic fibers while vacuum was applied on the opposite side of the fabric to suck the excess fluid through the fabric. The solution was also sprayed onto a tissue paper. Both impregnated substrates were dried for 10 minutes at 110° C. Similar samples were prepared and were dried overnight at room temperature. The absorption characteristics of these impregnated substrates varied with the amount of solution applied thereto but all exhibited enhanced absorbency.

EXAMPLE 7

This example illustrates the importance of having at least 25% of the carboxyl groups (on a molar basis) converted to the salt form in the crosslinked polyelectrolyte.

A series of 12.5% by weight solutions of polyacrylic acid in water is prepared wherein the polyacrylic acid employed has a molecular weight of 400,000. The solutions are neutralized to varying degrees as shown in Table 4 below. The XAMA-7, a polyfunctional aziridine obtained from the Cordova Chemical Company, is employed as the crosslinking agent by adding an amount equal to 1% of the weight of the polyelectrolyte to the solution. A film is cast from the solution onto a silicon coated release paper. The film is dried for 10 minutes at 130° C. and then ground to pass through a 20 mesh screen. The absorption capacity is measured by following the procedure described in Example 1 and the results are reported in Table 4 below.

The same procedure is followed for another series with the exception that an 11.1%, by weight, aqueous solution of 200,000 molecular weight polymethacrylic acid is employed as the polyelectrolyte. The results are also reported in Table 4 below.

TABLE 4

| Acid Type | pH | % Carboxyl in Salt Form | Absorbency gm/gm |
|---|---|---|---|
| Polyacrylic | 3 | 0 | 4 |
|  | 5 | 30 | 35 |
|  | 7 | 85 | 56 |
| Polymethacrylic | 3.5 | 0 | 3 |
|  | 5.0 | 25 | 30 |
|  | 7.5 | 85 | 37 |

As can be seen from the above table, as the percentage of carboxyl groups converted to the salt form increases beyond about 25% there is a marked increase in the absorbency.

EXAMPLE 8

This example illustrates the advantages of employing the aziridinyl crosslinking agents to prepare the products of this invention, as contrasted with the materials prepared by the teachings of U.S. Pat. No. 4,310,593 mentioned above.

Following the procedure of U.S. Pat. No. 4,310,593 an amine/epichlorohydrin adduct crosslinker was prepared by dissolving one gram of diethylenetriamine in 16 ml. of methanol. To this was added, with mixing, 1.8 grams of epichlorohydrin. The mixture, in a sealed bottle, was placed in a 65° C. water bath for one hour. A series of samples were prepared wherein the crosslinking reactions were carried out using an aqueous solution containing 12.5% by weight of a 400,000 molecular weight polyacrylic acid obtained from the Rohn Haas Company and sold by them under the trademark Acrysol A-5. In all cases the solution was neutralized to a pH of 7 and crosslinked with the amount of various crosslinking agents illustrated in Table 5 below, as expressed as weight % of crosslinking agent, based on the total weight of the neutralized acid. A 30 mil film was cast on release paper and allowed to dry, at room temperature for 18 hours. The resulting material was tested for absorbency in accordance with the test described in Example 1. The results are reported in the Table 5 below.

TABLE 5

| Crosslinking Agent (weight %) | Absorbency (gm/gm) | | |
|---|---|---|---|
|  | XAMA-2 | TAZ-O | Amine Epichlorohydrin |
| 0.5 | 31 | — | Soluble Polymer |
| 1.0 | 26 | 29 | Soluble Polymer |

As can be seen, the amine/epichlorohydrin adduct is not reactive enough to crosslink to a sufficient degree under these conditions.

EXAMPLE 9

This example illustrates the surprisingly greater reactivity of the crosslinking agents taught by this invention in making the products taught herein. The same neutralized acid employed in Example 8 in a 6% by weight, aqueous solution was mixed with 1% by weight of various crosslinkers, based on the weight of the neutralized acid and cured at 25° C. The time for gelation was recorded.

TABLE 6

| Crosslinker | Gelation Time |
|---|---|
| TAZ-O | 45 Minutes |
| XAMA-2 | 3 Hours |

TABLE 6-continued

| Crosslinker | Gelation Time |
| --- | --- |
| Amine/Epichlorohydrin | 72 Hours |

EXAMPLE 10

The same aqueous mixtures of neutralized acid and 1% crosslinker employed in Example 9 were used to treat 15 denier polyester fibers to attempt to render them absorbent and usable in absorbent products and, in particular, products for absorbing body fluids. The polyester fibers were dipped into the solution and excess solution was removed to the point that the remaining solution corresponded to a 50% weight gain of solution based on the weight of the dry fibers; i.e., 0.5 grams of solution per gram of dry fiber. Samples of the fibers were dried and the polyelectrolyte cured, at room temperature for three hours and for 18 hours. The absorbency of the samples for both water and a 1% by weight aqueous NaCl solution, was tested using the method of Example 1.

TABLE 7

| Crosslinking Agent | Absorbency gm/gm | | | |
| --- | --- | --- | --- | --- |
| | 3 Hours | | 18 Hours | |
| | Water | 1% NaCl | Water | 1% NaCl |
| XAMA-2 | 30 | 9 | 33 | 12 |
| Amine/Epichlorohydrin | 4.5 | 1.7 | 5 | 5 |

EXAMPLE 11

Twenty grams of the 12.5% solution of polyacrylic acid of Example 8 are neutralized with 2 grams of potassium carbonate and 0.5 grams of ammonium bicarbonate. The carbon dioxide generated in this reaction foamed the system. The foamed system is crosslinked with 1% TAZ-O crosslinking agent, based on the weight of the neutralized acid, for one minute in a microwave oven and for an additional three minutes at 110° C. in a hot air oven. When tested by the method of Example 1, the resulting cellular, fluffy material absorbed 400 grams of water per gram of material and 55 grams of 1% aqueous NaCl solution per gram of material in 30 seconds without further grinding. The same procedure was followed using, as the crosslinking agent, the amine/epichlorohydrin adduct. Gelation was slow and no cellular material was formed. The product absorbed only 10 grams of NaCl per gram of material after 30 seconds.

What is claimed is:

1. In a product for absorbing body fluids, an absorbent element comprising:
the reaction product of reactants comprising a water soluble carboxylic polyelectrolyte and a crosslinking agent comprising a water soluble, relatively low molecular weight compound containing at least two 1-aziridinyl groups, said reaction product having at least 25% of said carboxyl groups, on a molar basis, converted to the salt form.

2. The product of claim 1 wherein said 1-aziridinyl groups have the formula:

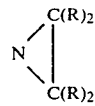

wherein each R group is independently selected from the group consisting of H, alkyl having from one to three carbon atoms, or alkenyl having from two to three carbon atoms.

3. The product of claim 1 wherein said compound has a molecular weight of less than 1000.

4. The product of claim 1 wherein said functional groups are bonded to aliphatic or substituted aliphatic groups which are sufficiently small enough to maintain the compound soluble in water.

5. The product of claim 1 wherein said compound is a difunctional aziridine.

6. The product of claim 1 wherein said compound is a tri-functional aziridine.

7. The product of claim 6 wherein said tri-functional aziridine is:

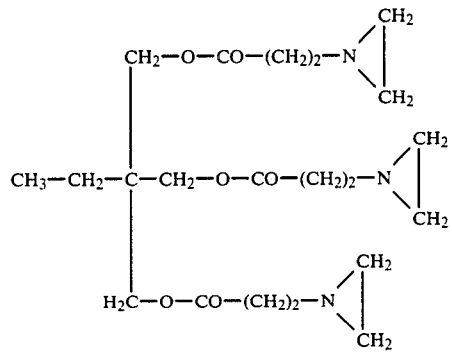

8. The product of claim 6 wherein said tri-functional aziridine is:

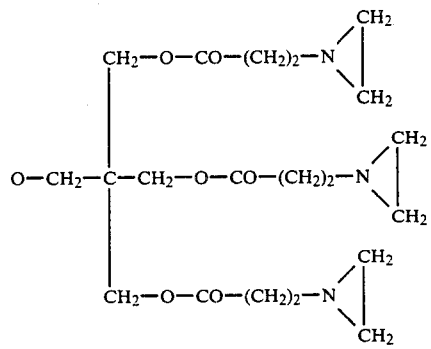

9. The product of claim 1 wherein said polyelectrolyte has a molecular weight of from 10,000 to 4,000,000.

10. The product of claim 1 wherein said compound is present in an amount of from about 0.2% to about 20%, by weight, based on the weight of the polyelectrolyte.

11. The product of claim 1 wherein said compound is present in an amount of from about 0.5 to about 15% by weight based on the weight of the polyelectrolyte.

12. The product of claim 1 wherein the compound is present in an amount of from about 1% to about 10% by weight based on the weight of the polyelectrolyte.

13. A method of preparing a water absorbent polyelectrolyte comprising the steps of:
   forming a composition by combining 1) a solvent selected from the group consisting of water, lower alcohols, and mixtures thereof with 2) about 5 to 60% by weight of carboxylic polyelectrolyte or mixtures thereof and 3) a crosslinking agent comprising a water soluble, relatively low molecular weight compound having at least two 1aziridinyl groups bonded thereto;
   crosslinking said carboxylic polyelectrolyte with said crosslinking agent, neutralizing said crosslinked polyelectrolyte to a degree sufficient for at least 25% of said carboxyl group, on a molar basis, to be converted to the salt form and drying the resultant product.

14. The method of claim 13 wherein said 1-aziridinyl groups have the formula:

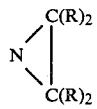

wherein each R group is independently selected from the group consisting of H, alkyl having from one to three carbon atoms, or alkenyl having from two to three carbon atoms.

15. The method of claim 13 for preparing said absorbent polyelectrolyte in the form of a film comprising spreading said composition on an impervious substrate and then crosslinking and drying said composition.

16. The method of claim 13 for preparing said water absorbent polyelectrolyte as a foam comprising including in said composition a neutralizing base capable of releasing gas upon neutralizing.

17. The method of claim 16 wherein said neutralizing base is a carbonate compound.

18. The method of claim 17 wherein said carbonate compound is selected from the group consisting of sodium carbonate, potassium carbonate, or ammonium bicarbonate.

19. A method of preparing a water absorbent polyelectrolyte comprising the steps of:
   forming a composition by combining
   (1) a solvent selected from the group consisting of water, lower alcohols, and mixtures thereof with
   (2) about 5 to 60%, by weight, of carboxylic polyelectrolyte having at least 25% of said carboxylic groups, on a molar basis, converted to the salt form; and
   (3) a crosslinking agent comprising a water soluble, relatively low molecular weight compound containing at least two 1-aziridinyl groups;
   crosslinking said carboxylic polyelectrolyte with said crosslinking agent; and drying the resultant product.

20. The method of claim 19 wherein said 1-aziridinyl groups have the formula:

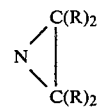

wherein each R group is independently selected from the group consisting of H, alkyl having from one to three carbon atoms, or alkenyl having from two to three carbon atoms.

21. The method of claim 19 for preparing said absorbent polyelectrolyte in the form of a film comprising spreading said composition on an impervious substrate and then crosslinking and drying said composition.

22. The method of claim 19 for preparing said water absorbent polyelectrolyte as a foam comprising including in said composition a neutralizing base capable of releasing gas upon neutralizing.

23. The method of claim 22 wherein said neutralizing base is a carbonate compound.

24. The method of claim 23 wherein said carbonate compound is selected from the group consisting of sodium carbonate, potassium carbonate, or ammonium bicarbonate.

* * * * *